United States Patent
Rowland et al.

(10) Patent No.: US 9,867,552 B2
(45) Date of Patent: Jan. 16, 2018

(54) IMPLANTABLE SENSOR ENCLOSURE WITH THIN SIDEWALLS

(75) Inventors: Harry D. Rowland, Plainfield, IL (US); Michael Nagy, Lawrenceville, GA (US)

(73) Assignee: ENDOTRONIX, INC., Lisle, IL (US)

(*) Notice: Subject to any disclaimer, the term of this patent is extended or adjusted under 35 U.S.C. 154(b) by 464 days.

(21) Appl. No.: 14/129,725

(22) PCT Filed: Jun. 29, 2012

(86) PCT No.: PCT/US2012/044998
§ 371 (c)(1),
(2), (4) Date: Feb. 21, 2014

(87) PCT Pub. No.: WO2013/003754
PCT Pub. Date: Jan. 3, 2013

(65) Prior Publication Data
US 2014/0155710 A1  Jun. 5, 2014

Related U.S. Application Data

(60) Provisional application No. 61/502,982, filed on Jun. 30, 2011.

(51) Int. Cl.
*A61B 5/02* (2006.01)
*A61B 5/07* (2006.01)
*A61B 5/00* (2006.01)
*A61B 5/0215* (2006.01)

(52) U.S. Cl.
CPC .......... *A61B 5/076* (2013.01); *A61B 5/0215* (2013.01); *A61B 5/6861* (2013.01)

(58) Field of Classification Search
None
See application file for complete search history.

(56) References Cited

U.S. PATENT DOCUMENTS

| | | | |
|---|---|---|---|
| 4,026,276 A | 5/1977 | Chubbuck | |
| 5,454,270 A | 10/1995 | Brown et al. | |
| 5,510,276 A * | 4/1996 | Diem | B81C 1/00158 148/DIG. 135 |
| 5,840,148 A * | 11/1998 | Campbell | A01K 11/007 156/275.5 |
| 6,939,299 B1 | 9/2005 | Petersen et al. | |

(Continued)

FOREIGN PATENT DOCUMENTS

| CA | 2840645 A1 | 1/2013 |
|---|---|---|
| CN | 1701464 A | 11/2005 |

(Continued)

OTHER PUBLICATIONS

Extended European Search Report, Application No. 12804636.4-1660 / 2725969, Endotronix, Inc., Jan. 20, 2015.
(Continued)

*Primary Examiner* — Navin Natnithithadha
*Assistant Examiner* — Michael R Bloch
(74) *Attorney, Agent, or Firm* — McDonald Hopkins LLC

(57) ABSTRACT

A wireless circuit includes a housing, such as a hermetic housing, and at least one antenna coil wound about a coil axis within the housing. The coil axis may be substantially parallel to at least one wall of the housing, wherein the wall parallel to the coil axis is substantially thinner than other walls of the housing.

14 Claims, 7 Drawing Sheets

Side View

Front View (Cutaway)

(56) References Cited

U.S. PATENT DOCUMENTS

| | | |
|---|---|---|
| 7,174,212 B1 | 2/2007 | Klehn et al. |
| 7,401,521 B2 | 7/2008 | Bellini et al. |
| 7,574,792 B2 | 8/2009 | O'Brien et al. |
| 7,686,762 B1 * | 3/2010 | Najafi .................. A61B 5/0031 600/300 |
| 7,763,487 B2 | 7/2010 | Villa et al. |
| 8,132,465 B1 | 3/2012 | Doelle et al. |
| 8,154,389 B2 | 4/2012 | Rowland et al. |
| 8,493,187 B2 | 7/2013 | Rowland et al. |
| 9,305,456 B2 | 4/2016 | Rowland et al. |
| 2006/0109188 A1 | 5/2006 | Ikeda et al. |
| 2006/0177956 A1 | 8/2006 | O'Brien et al. |
| 2006/0241354 A1 | 10/2006 | Allen |
| 2006/0287602 A1 | 12/2006 | O'Brien et al. |
| 2007/0163355 A1 | 7/2007 | Nassar et al. |
| 2007/0208390 A1 | 9/2007 | Von Arx et al. |
| 2007/0267708 A1 | 11/2007 | Courcimault |
| 2008/0269573 A1 | 10/2008 | Najafi et al. |
| 2008/0269829 A1 | 10/2008 | Li et al. |
| 2009/0221885 A1 | 9/2009 | Hall et al. |
| 2011/0004076 A1 * | 1/2011 | Janna .................. A61B 5/0031 600/302 |
| 2011/0046452 A1 | 2/2011 | Najafi et al. |
| 2011/0063088 A1 | 3/2011 | Stevenson et al. |
| 2014/0028467 A1 | 1/2014 | Nagy et al. |
| 2014/0306807 A1 | 10/2014 | Rowland et al. |

FOREIGN PATENT DOCUMENTS

| | | | |
|---|---|---|---|
| CN | 101128957 A | 2/2008 | |
| CN | 101278439 A | 10/2008 | |
| JP | 2000005136 A | 1/2000 | |
| JP | 2002515278 A | 5/2002 | |
| JP | 2003144417 A | 5/2003 | |
| JP | 2005284511 A | 10/2005 | |
| JP | 2006309582 A | 11/2006 | |
| JP | 2007256287 A | 10/2007 | |
| JP | 2008022935 A | 2/2008 | |
| JP | 2010538254 A | 12/2010 | |
| WO | 2009146089 A1 | 12/2009 | |
| WO | 2012015955 A1 | 2/2012 | |
| WO | WO 2013003754 A1 * | 1/2013 | ........... A61B 5/6861 |

OTHER PUBLICATIONS

Extended European Search Report for Application 14806873.7 PCT/US2014030661, dated May 20, 2016, 7 pp., European Patent Office, Germany.

Patent Cooperation Treaty (PCT), International Search Report and Written Opinion for Application PCT/US/14/30661, dated Sep. 17, 2015, 8 pp., International Searching Authority, US.

Patent Cooperation Treaty (PCT), International Search Report and Written Opinion for Application PCT/US12/44998, dated Sep. 25, 2012, 9 pgs., International Searching Authority, US.

IL Notification No. 25, Notification of Defects in Patent Application No. 230193 in Israel, dated Jan. 26, 2017, State of Israel Ministry of Justice, The Patent Office.

* cited by examiner

SIDE VIEW

FRONT VIEW
(CUTAWAY)

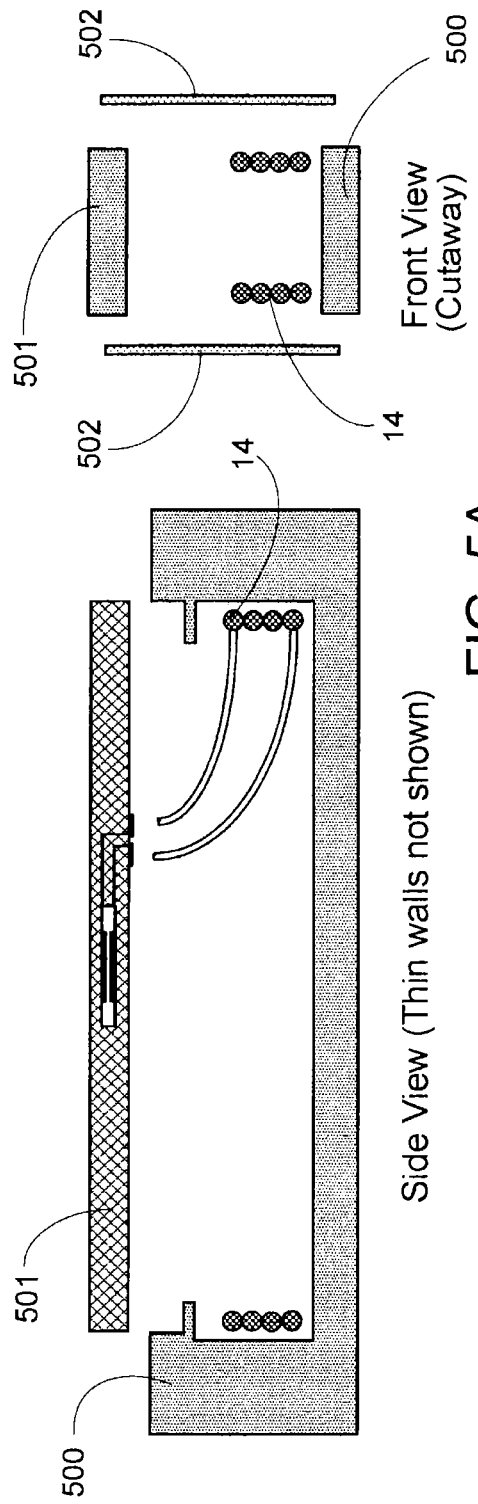
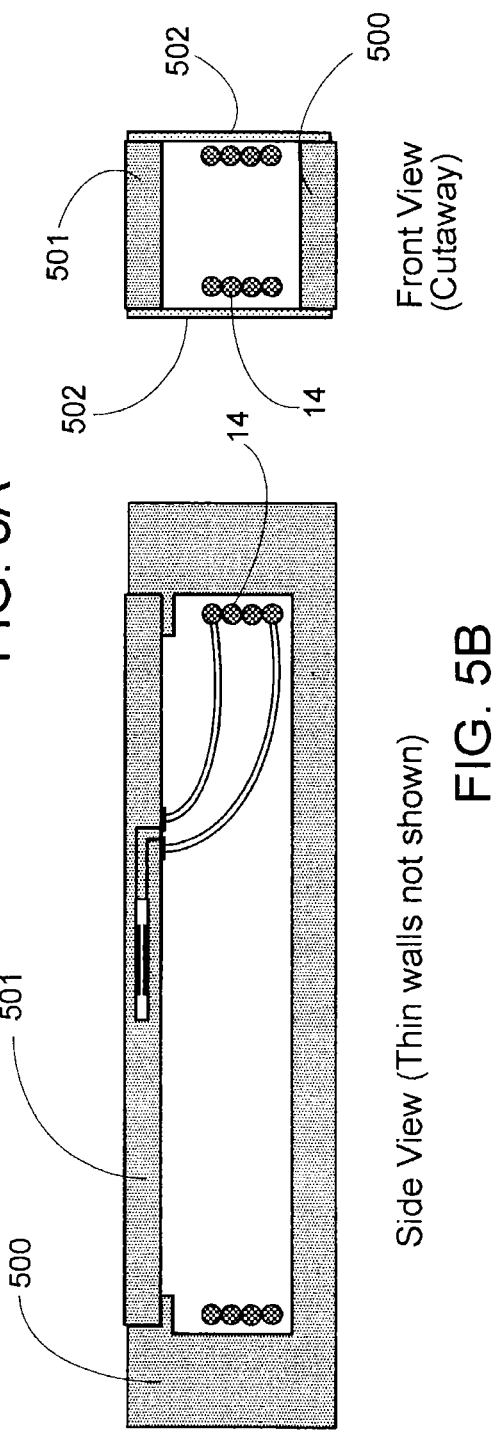
FIG. 5A
FIG. 5B

IMPLANTABLE SENSOR ENCLOSURE WITH THIN SIDEWALLS

CROSS-REFERENCE TO RELATED APPLICATIONS

This application claims priority to PCT Application PCT/US2012/044998 entitled "IMPLANTABLE SENSOR ENCLOSURE WITH THIN SIDEWALLS" filed on Jun. 29, 2012 which claims benefit of Provisional Patent Application No. 61/502,982 entitled "IMPLANTABLE SENSOR ENCLOSURE WITH THIN SIDEWALLS," filed on Jun. 30, 2011, which are hereby incorporated by reference in its entirety

FIELD OF INVENTION

This application relates to implant packages and more particularly to an implantable sensor enclosure with thin sidewalls.

BACKGROUND

Implantable wireless sensors are useful in assisting diagnosis and treatment of many diseases. Examples of wireless sensor readers are disclosed in U.S. patent application Ser. No. 12/737,306 entitled Wireless Sensor Reader, which is incorporated by reference herein. Delivery systems for wireless sensors are disclosed in PCT Patent Application No. PCT/US2011/45583 entitled Pressure Sensor, Centering Anchor, Delivery System and Method, which is also incorporated herein by reference. In particular, there are many applications where measuring pressure from within a blood vessel deep in a patient's body is clinically important. For example, measuring the pressure in the heart's pulmonary artery is helpful in optimizing treatment of congestive heart failure. In this type of application, a sensor may need to be implanted 10 to 20 cm beneath the surface of the skin.

Wireless sensors that use radiofrequency (RF) energy for communication and/or power have been found to be particularly useful in medical applications. However, a key challenge in successful commercialization of these implantable wireless sensors is the design tradeoff between implant size and the "link distance", which is the physical distance between the implant and the external device communicating with the implant. From a medical standpoint, it is desirable for an implant to be as small as possible to allow catheter based delivery from a small incision, implantation at a desired location, and a low risk of thrombosis following implant. However, from a wireless communication standpoint, the smaller the implant, the shorter the link distance. This distance limitation is driven primarily by the size of the antenna that can be realized for a given overall implant size. A larger antenna is better able to absorb RF energy and transmit RF energy than a smaller antenna. For example, in the case of wireless communication via inductive coupling, a typical implant antenna has the form of a coil of wire. The coil's "axis" is the line that extends normal to the plane of the windings, i.e. the axis is perpendicular to the wire's length. As the area encircled by the coil increases, the amount of magnetic flux that passes through it generally increases and more RF energy is delivered to/received from the implant. This increase in flux through the implant antenna can result in an increase in link distance. Thus to achieve maximum link distance for a given implant size, the implant antenna should be of maximal size.

While antenna size is important, other implant architectures may benefit from maximizing the size of other internal components. An implant containing an energy storage device such as a battery, for example, would enjoy longer battery lifetime with a larger battery. In another example, a drug-eluting implant could hold a larger quantity of the drug. Other examples will be apparent to those skilled in the art.

Another challenge in commercialization of implantable wireless sensors is the need to protect the sensitive sensor electronics from potentially corrosive or damaging fluids of the body. For many implant applications, the sensor may need to record accurate measurements for a period of time exceeding 7 to 10 years. Small changes in electrical, chemical, or mechanical properties of the implant over this time period can result in inaccurate measurements. To prevent inaccurate measurements, a hermetic enclosure may be required to protect the sensitive electronics of the sensor from the transfer of liquids and gases from the bodily environment.

Hermetic enclosures for implants are typically constructed of metals, glasses, or other ceramics. Metals are malleable and machineable, capable of being constructed into thin walled hermetic enclosures such as the titanium enclosures of pacemakers. Unfortunately, the use of metals in hermetic enclosures may negatively impact the ability of the sensor to communicate wirelessly with an external device, especially when communication at low radiofrequencies is desired. While ceramics and glasses are compatible with wireless RF communication, it is difficult to machine ceramics to a thin walled hermetic enclosure. The brittleness of ceramics prevents the construction of thin wall hermetic enclosures from ceramic materials.

State of the art ceramic machining can produce walls of approximately 0.5-0.7 mm thickness. For implants whose length, width, and height dimensions are typically ones of millimeters, this can represent a significant reduction in available internal volume for components such as antennas.

Hermetic enclosures known in the art, particularly those made of ceramic and/or glass materials, do not lend themselves to efficient use of limited space. Non-metal hermetic enclosures known in the art are typically manufactured via planar processing technology, such as low temperature cofired ceramic processes, laser machining, ultrasonic machining, Electronic Discharge Machining (EDM), or Micro Electro Mechanical Systems (MEMS) fabrication techniques. These techniques are capable of processing ceramics and glasses with tight control of feature resolution. However, sidewalls of an implant package made with these techniques often require use of a dicing saw or laser to separate the implant package from the remaining substrate. Due to manufacturing constraints and the need for mechanical strength, implant package sidewalls made by these methods are typically 0.3 mm-0.5 mm thick. Alternative manufacturing approaches, such as the molding or machining of ceramic, are typically limited to minimum sidewalls of 0.5-0.7 mm thick.

An example of a prior art hermetic implant package 10 is shown in FIG. 1. The implant package 10 includes thick sidewalls 12 that limit the space available for the internal components, in this case implant antenna 14. For example, an implant package of width 4 mm that has sidewalls 0.5 mm thick only has a maximum of 3 mm of width available for an implant antenna. FIG. 1 shows an antenna 14 that is placed into the implant package from an opening at the top of the package. To complete the implant package, a top layer 16 is connected or bonded to the implant package and sealed as shown in FIG. 2A. For pressure-sensing implant packages known in the art, the top layer is typically either a capacitive pressure sensor itself, a thin membrane that is directly part of a sensing electronic circuit, or a thin membrane that communicates pressure from the environment to the inside of the implant package via an incompressible liquid or gel. Manufacturing techniques known in the art are capable of routinely processing membranes to thicknesses of 0.025-0.1 mm. Many variations of the FIG. 1-2 architecture exist in the prior art, including the method of etching a cavity in half of a housing to create the thin wall on top of the coil, and then bonding the two housing halves vertically. This is depicted in the sketch of FIG. 2B, where the upper housing half 999 has a cavity etched into it to create the thin membrane.

Other prior art exemplifies wireless implant architectures of the type shown in FIG. 1 and FIG. 2, where the thin pressure sensitive membrane is in a plane that is perpendicular to the coil's axis. U.S. Pat. No. 7,574,792 (O'Brien), U.S. Pat. No. 6,939,299 (Petersen), and U.S. Pat. No. 4,026,276 (Chubbuck) all teach implantable pressure sensors with coil antennas, and hermetic housings with at least one deformable pressure-sensitive wall. In all these cases, the pressure-sensitive walls of the housings are perpendicular to the coil axis, and the walls located outside the coil perimeter are rigid, structural, and relatively thick. In these architectures, total coil area is limited by the need for a relatively thick structural wall outside the coil perimeter.

To improve implantable wireless sensors, it is desirable to have a hermetic enclosure with thin walls outside the coil antenna perimeter, thus maximizing the internal dimension that most constrains antenna size.

SUMMARY OF THE INVENTION

This application relates to hermetically packaged wireless electronics and more particularly to implantable electronics enclosures with thin sidewalls to maximize an internal dimension.

In an embodiment, a wireless circuit includes a housing and at least one antenna coil wound about a coil axis within the housing. The coil axis may be substantially parallel to at least one wall of the housing, wherein the wall parallel to the coil axis is substantially thinner than other walls of the housing. The housing may be a hermetically sealed housing.

In an embodiment, the wireless circuit may be manufactured by forming a housing of a material with at least one open side. Electronics, including an antenna coil, may then be placed into the housing such that said antenna coil's axis is substantially parallel to the plane of at least one open side. A wall that is substantially thinner than the walls of the housing may then be bonded to the open side. The wall may be hermetically bonded or otherwise bonded as known in the art.

BRIEF DESCRIPTION OF THE DRAWINGS

Embodiments of the present disclosure are described herein with reference to the drawings wherein:

FIG. 5A is an exploded sketch of another alternative embodiment of the present invention, with electronics bonded to the top of the housing;

FIG. 5B illustrates the completed alternative embodiment of the present invention, with electronics bonded to the top of the housing;

DETAILED DESCRIPTION OF THE PREFERRED EMBODIMENTS

Reference will now be made in detail to embodiments of the invention, examples of which are illustrated in the accompanying drawings. It is to be understood that other embodiments may be utilized and structural and functional changes may be made without departing from the respective scope of the invention.

This application relates to implant packages and more particularly to an implantable sensor enclosure with thin sidewalls. To facilitate maximum link distance for a given implant size, the enclosure should be constructed to maximize antenna coil area, while still providing ample protection.

Figure 1:
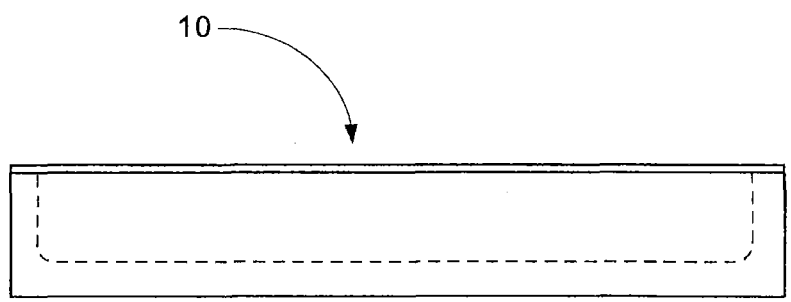
FIG. 1 illustrates a prior art implant package, not including the final sealing layer.
Figure 1:
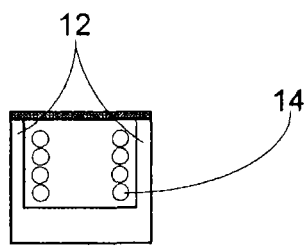
Figure 2A:
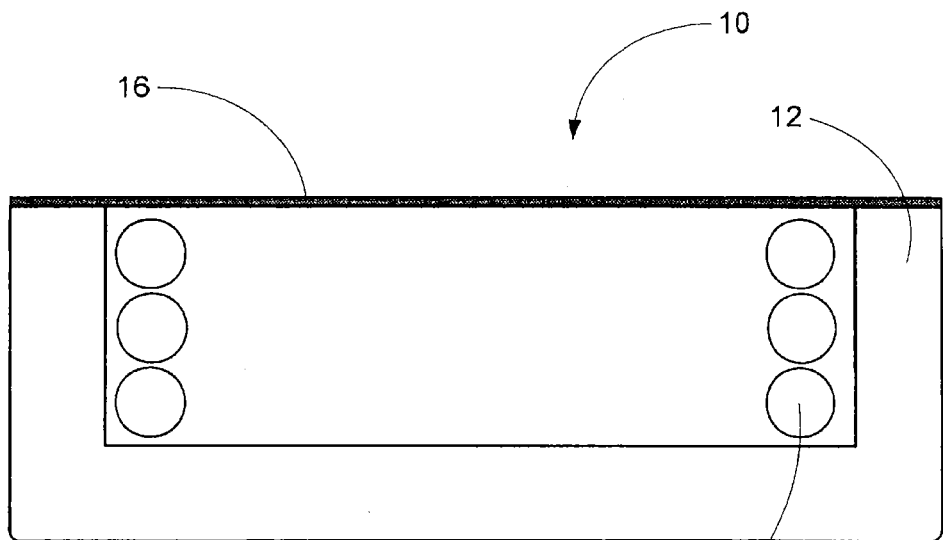
FIG. 2A illustrates a typical prior art implant package, including a thin sealing layer.
Figure 2B:
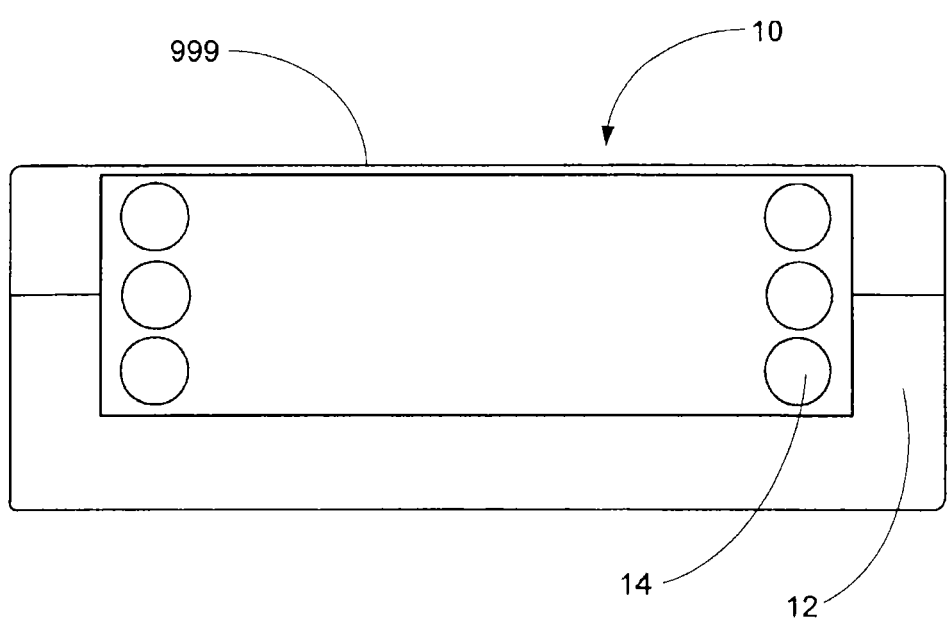
FIG. 2B illustrates a typical prior art implant package, with a cavity etched into part of the housing.

The implant package may utilize thin membrane materials such as glass, quartz, sapphire, fused silica, alumina, titanium, diamond, or other materials known in the art, to increase the space available inside an implant package of a fixed outer size. Whereas in prior art implant packages the thin membrane is bonded to the top of the implant package, as in FIGS. 1 and 2, the thin membrane or membranes may be bonded to the side of the implant package, such that they are in a plane substantially parallel with the axis of the coil, as in FIG. 3.

Figure 3A:
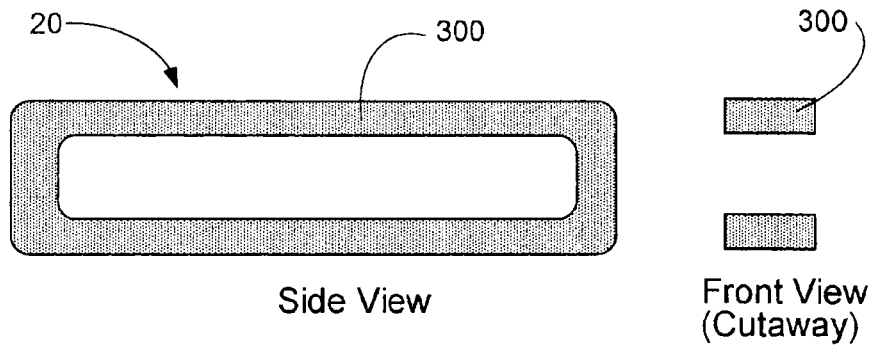
FIG. 3A illustrates the housing portion of a hermetic wireless package of the present invention.
Figure 3B:
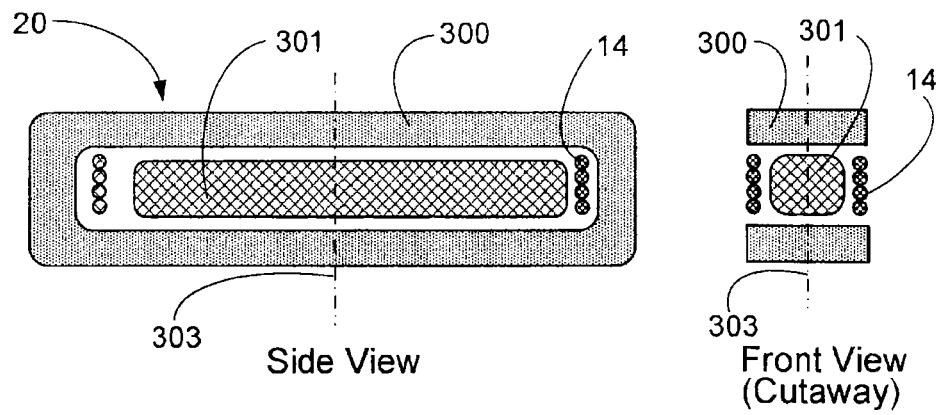
FIG. 3B illustrates the complete hermetic wireless implant of the present invention.
Figure 3C:
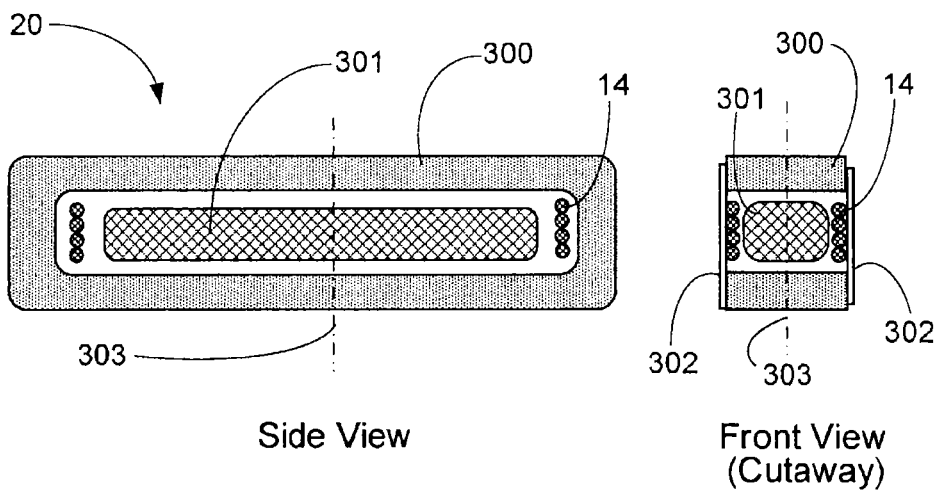

FIGS. 3A-3C show basic assembly steps for a wireless implant package 20 that maximizes coil area by its wall arrangement. The implant in the Figure has the long, narrow, rectangular shape of a typical cardiovascular implant, although the principle applies to any geometry. FIG. 3A illustrates the basic housing 300 in side view (long dimension) and front view (short dimension) cutaway. In an embodiment, the dimension of housing 300 may be generally cuboid and defining a volume therein. The housing side walls may be of specific dimensions and proportions to each other. For example, the housing may have four walls ('top', 'bottom', 'front', and 'back'), but two of the long sides may be open, so that one can look through the housing into the page in the FIG. 3A side view. As described herein, the length of the housing side walls refers to the longer dimension of the open walls (also corresponding to the longer dimension of the top and bottom walls of the housing as illustrated in the Side View of FIG. 3A.) The height and width of the housing refers to the dimensions of the remaining sidewalls or the top and bottom walls as illustrated in the Front view of FIG. 3A. Dimensions provided below list the dimensions of the housing in the order of (length×width×height). The length of the housing may be at least two-times greater than the width and height dimensions. By way of a non-limiting example, the dimensions of the housing may be approximately 25×3.75×2.25 mm, with walls 0.5 mm thick. Housing 300 may be made of a hermetic, strong, and biocompatible material, such as ceramic. Such housings are fabricated with processes well known in the art, including micromachining, ultrasonic machining, wet etching, plasma etching, or laser machining. While examples are made to a cuboid housing, it will be appreciated that other shapes and configurations may be used, such as cylindrical housings, prism-shaped housings, octagonally or hexagonally cross-sectioned housings, or the like.

In other embodiments the length of the implant housing may have values of 5, 10, 15, 20, 25, or 30 mm long. The cross sections may have width×height values of 5×3 mm, 4.5×2.25 mm, 3.25×2.25 mm, 2.5×1.75 mm, or 2×1 mm.

In FIG. 3B, an antenna coil 14, also shown in cutaway, is placed into the housing 300 via the open walls on the long side. Microelectronics 301, which may include one or more pressure sensors, may also be placed inside housing 300, inside the region encircled by coil 14, or outside of this region.

FIG. 3C depicts the final step, in which thin walls 302 are bonded to housing 300, such as hermetically bonded. It will be appreciated that the thin walls 302 may be sealed or bonded in any appropriate manner. It will also be appreciated that the concepts herein may apply to non-hermetic housing applications, such as acute implants. In these cases, non-hermetic materials and bonding methods known in the art may be used. As illustrated and described in the examples herein, the thin walls 302 may be substantially thinner, or include a portion that is substantially thinner, than the remaining walls of the housing. Non-limiting examples of wall thicknesses of the housing walls and thin walls 302 are provided below. By orienting the thin walls 302 such that they are parallel to the axis 303 of coil 14, the width of coil 14 in the short dimension (left to right in the front view) is maximized. In this way, the implant package can achieve the maximum possible coil loop area within the width constraint imposed on the short dimension. It will be appreciated that the coil axis 303 refers to the central axis of a generally spirally wound coil 14, as shown in FIG. 3. The spirally wound coil 14 may be any appropriate shape, such as circular, rectangular, or any other shape.

The final implant produced by the process of FIG. 3 meets the complex requirements of medical implants: (i) small cross-sectional area, (ii) non-metal housing, (iii) hermetic sealing, (iv) biocompatibility, and (v) maximum internal volume for a given external volume.

In the case where wireless implant 20 contains a pressure sensor, internal electronics 301 may include one or more pressure sensors known in the art, and thin walls 302 may be flexible membranes which communicate pressure to internal electronics 301 by means of an incompressible fluid or gel that fills the cavity formed by housing 300 and thin walls 302. In another embodiment, the thin walls 302 may be flexible membranes which are part of a sensing electronic circuit, thus transducing pressure directly into an electronic signal of a sensing circuit.

The walls of the housing other than the thin walls 302 may be greater than 0.3 mm. By comparison, in an embodiment, by using membranes as the thin sidewalls 302 of the implant package 20 each sidewall may have a thickness of less than 0.15 mm. In another embodiment, by using membranes as the thin sidewalls 302 of the implant package 20 each sidewall may have a thickness less than about 0.050 mm. In another embodiment, by using membranes as the thin sidewalls 302 of the implant package 20 each sidewall may have a thickness of about 0.025 mm. In another embodiment, by using membranes as the sidewalls of the implant package 302 each sidewall may have a thickness less than about 0.025 mm, such as about 0.020 mm, about 0.015 mm, about 0.010 mm, about 0.005 mm, about 0.001 mm and any sized thickness in between. Thus, the thin walls 302 may have one half or less of the thickness of the non-thin walls of the housing 20.

In a typical embodiment, thin walls 302 may be made of one or more thin film materials such as glass, quartz, fused silica, titanium, silicon, sapphire, diamond, or others. It may be thinned by polishing, etching, or other methods well known in the art. Thin walls 302 may be bonded to housing 300 by several means known in the art, including laser welding, glass frit bonding, or compression bonding by brazing, soldering, or eutectic bonding, following deposition of a metal braze ring on the two surfaces.

For bonding technologies that require a metal ring to be deposited around the perimeter of each diaphragm, on both the diaphragm and mating surfaces on the housing, the architecture of FIG. 3C provides a further advantage over the prior art. When the metal ring is parallel to the antenna windings, as in prior art FIG. 1, it may absorb and dissipate significant amounts of energy going to and coming from the antenna 14, due to shielding and eddy current formation. However, when the diaphragm bonding rings are arranged perpendicular to the antenna windings as in FIG. 3C, the shielding and eddy current effects are practically eliminated.

The thin-walled housing or implant package 20 provides a significant improvement in the efficient use of space inside an implant package over prior art. By way of a non-limiting example, for a prior art implant package having an outer width of about 4 mm, the maximum available width for the antenna was approximately 3 mm. By contrast, in a thin-walled implant package 20 with an outer width of about 4 mm, the available width for the antenna is approximately 3.95 mm. Such an increase in antenna width for a given implant outer size may dramatically increase the wireless link distance of an implantable wireless sensor. This difference in antenna width of the thin-walled implant package 20 can translate into a catheter delivery system that is about 3 Fr sizes smaller for the present invention than for prior art systems.

The invention is thus particularly useful in wireless implants that have one axis longer than the others, which is generally the case for implants that are intended for placement in blood vessels, or intended for delivery through a catheter device. If the ratio of length to width of such an implant is x, then increasing the coil's width dimension by n microns creates more coil area than the same increase in the length dimension, by a factor of x. In such wireless implants, one can generally maximize coil area by placing the thinnest sidewalls parallel to the coil axis, and perpendicular to the shorter dimension, as in FIG. 3C.

It will be further appreciated that the implant architecture can be used to maximize the size of any internal component, substance, or combination thereof. These may include, but are not limited to, drugs, steroids, batteries, stimulus electrodes, pacing circuitry, flow sensors, chemical sensors, or other electronics.

It will be further appreciated that although the exemplary embodiments depict a rectangular coil, the coil 14 can be generally circular, ovular, rectangular, or can take the form of any polygon that encloses an area. Additionally, although a rectangular housing is shown in the exemplary embodiment figures, the concept of disposing the thin walls on the outer periphery of coil 14, parallel to coil axis 303, can be generalized to any polygonal shape.

The disclosed invention depicted in FIG. 3 may have a further benefit for pressure sensing implants. Many commonly available chip-scale pressure sensors are well suited for use in wireless implants. However, such pressure sensors generally have small, thin, pressure sensing diaphragms, on the order of 2 mm diameter or less and thickness of 500 nm or less. If such a diaphragm is exposed to living tissue or blood, one or more layers of cells will usually grow on it after a period of several days or weeks. Cell layers such as this are known to stiffen the sensor's diaphragm, decreasing the device's sensitivity. In the embodiment shown in FIG. 3C, the thin sidewalls 302 may serve as flexible pressure diaphragms, which communicate pressure to chip-scale pressure sensors on internal electronics 301 through a pressure-communicating medium. Because they are larger in area and generally stiffer than the diaphragms of chip scale sensors, the thin sidewalls 302 will not be stiffened significantly by several layers of cell growth, compared to the smaller diaphragms of the chip-scale sensors. Thus the present invention allows pressure sensor implant designers to select from a number of available off-the-shelf or custom chip-scale pressure sensors, without having to worry about diaphragm stiffening due to cell growth.

While the thin-walled implant package 20 may be used with RF medical implants, the designs set forth herein are useful for any micro device or component where a non-metal hermetic enclosure is required and where it is desirable to minimize sidewall thickness. Examples include, but are not limited to, sensors, actuators, or transponders located in harsh chemical environments, in liquid immersion, in high temperature zones (such as engines), or in environments where sterility is critical. Other examples include applications where the internal electronics must be hermetically housed, but cannot tolerate shielding or eddy current losses imposed by metal housings or braze rings. The designs and methods described herein overcome the many challenges associated with wireless sensors that use radiofrequency.

Figure 4A:
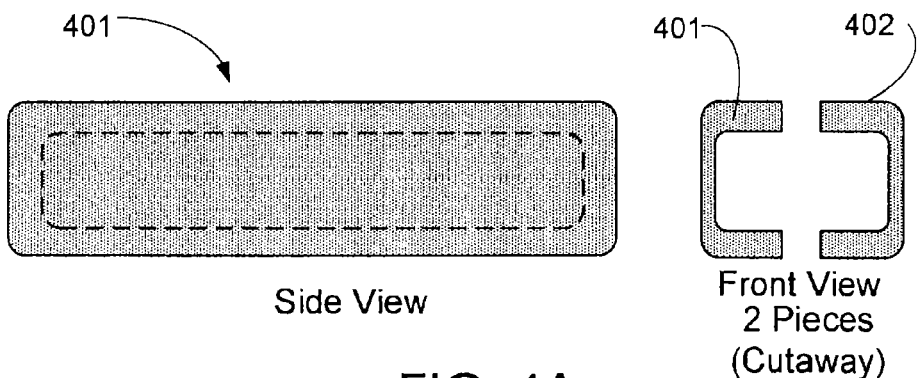
FIG. 4A illustrates the housing portion of an alternative embodiment of the present invention, with etched cavities and a split housing.
Figure 4B:
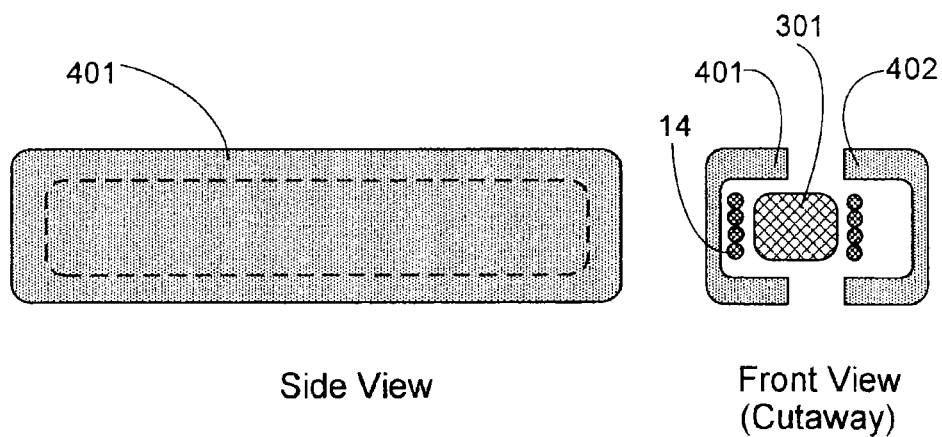
FIG. 4B illustrates the assembly of an alternative embodiment of the present invention, with etched cavities and a split housing.
Figure 4C:
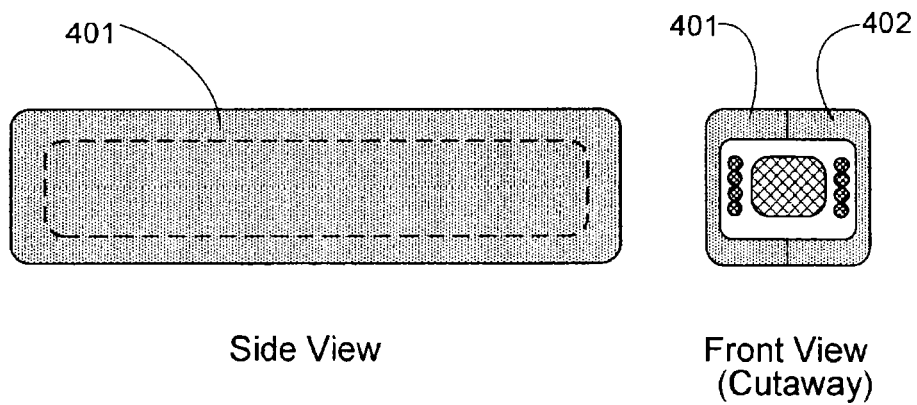
FIG. 4C illustrates the completed implant, for an alternative embodiment of the present invention, with etched cavities and a split housing.

There are also numerous variations of the embodiment shown in FIG. 3. For example, as shown in FIG. 4A, the housing is formed in two pieces 401 and 402, each with a cavity formed by one of the micromachining processes known in the art. The location of the cavity is shown as a dotted line in the side view, and can be seen in the cutaway. As shown in FIG. 4B, the coil 14, electronics 301, and other internals are inserted into one of the housing pieces 401. As shown in FIG. 4C, housing pieces 401 and 402 are bonded together hermetically by one of the methods previously disclosed. Note that in FIGS. 4A-4C, housing pieces 401 and 402 are shown as symmetrical, but asymmetrical pieces may also be employed.

FIGS. 5A and 5B depict an embodiment in which the electronics 501 are fabricated as a thin film device by one of the processes known in the art, with FIG. 5A being an exploded view and FIG. 5B showing all parts assembled. In FIGS. 5A and 5B, housing 500 has its long sides open as before, but this time its top side is open. Coil 14 is then inserted into housing 500. The thin film electronics device 501 is connected to coil 14 by wirebonding, conductive adhesive, or other means known in the art, and electronics 501 are then hermetically bonded to housing 500 using one of the aforementioned processes. Electronics 501 now forms the top surface of the housing. Thin sidewalls 502 are hermetically attached to housing 500 as before. If the thin electronics 501 contain a pressure sensor, the internal volume of the housing may not need to be filled with an incompressible fluid, as thin sidewalls 502 do not need to communicate pressure. Additionally, it will be appreciated that the steps of bonding electronics 501, bonding each of thin sidewalls 502, or inserting coil 14, may be done in a different order. The electronics 501 may be a single, solid state device, such as a capacitive sensor, or it may be multiple devices attached to a hermetic substrate such as LTCC.

Figure 6:
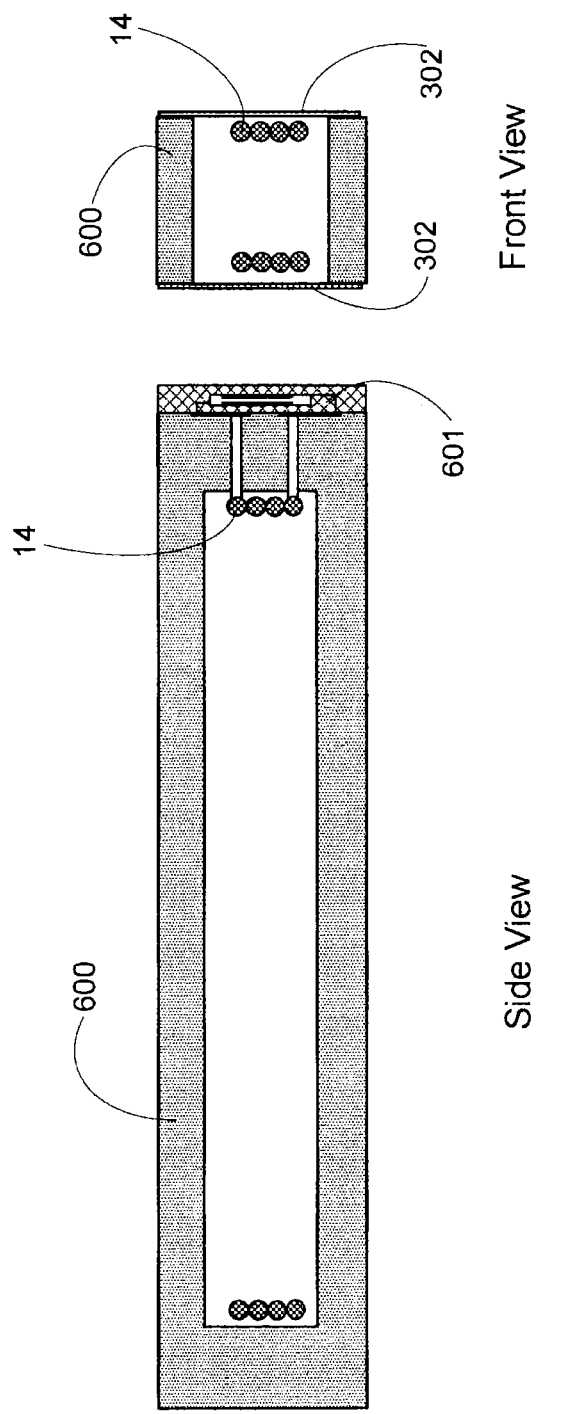
FIG. 6 illustrates another alternative embodiment of the present invention, with electronics bonded to the side of the housing.

FIG. 6 illustrates an embodiment similar to that of FIG. 5. The electronics 601 are placed on the exterior of housing 600, but this time on one of the short ends. FIG. 6 depicts hermetic electrical feedthroughs connecting electronics 601 to coil 14, but a 'free wire' connection method such as the one depicted in FIGS. 5A and 5B may also be employed. As in FIGS. 5A and 5B, the thin sidewalls 302 are not communicating pressure and so incompressible liquid fill may not be required.

Figure 7:
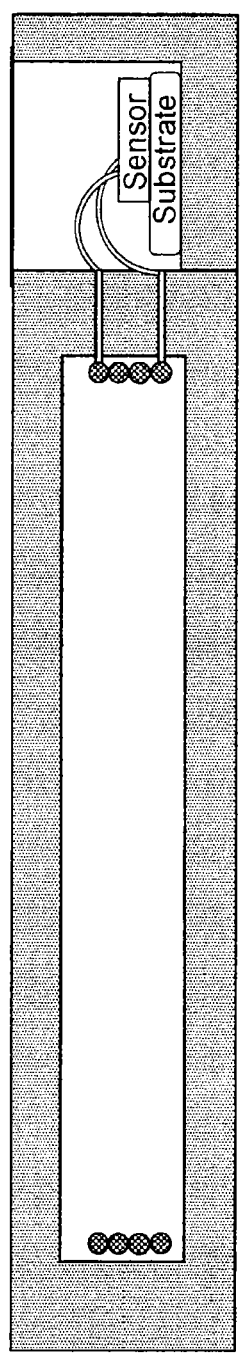
FIG. 7 illustrates another alternative embodiment of the present invention, with electronics contained in a separate housing chamber

FIG. 7 illustrates an embodiment similar to that of FIG. 6. Here the housing has two chambers, one for the coil and another for the electronics (shown here as "Sensor" and "Substrate"). The coil and electronics connect via a feedthrough that may or may not be hermetic. Thin sidewalls are placed in the usual place on the sides of the coil, and again over the chamber that contains the electronics. If the electronics does not contain a pressure sensor, the sidewall over the electronics chamber may be a thicker wall or a thin wall of a stiffer material. If the electronics contains a pressure sensor, and if the electrical feedthrough is sufficiently leak tight, then only the chamber containing the sensor needs to be filled with incompressible fluid.

The invention disclosed herein is particularly advantageous when the wireless implant is required to be long and narrow, as is typically the case with cardiovascular implants. With such geometries, any coil width gained in the short dimension has a dramatic impact on coil area and hence link distance.

Many of the embodiments disclosed herein may benefit from having the final sidewalls attached in a vacuum environment, to prevent internal pressures inside the housing from varying with temperature. Alternatively, the internal volume may be filled with an inert gas to limit corrosion of the internals.

It will also be appreciated that the implant housing embodiments disclosed herein can be made using all thick walls, and then post-processing the housing to thin portions of the walls that are parallel to the coil's axis. State of the art post-processing technologies such as grinding, polishing, etching, or laser ablation are some possible means for accomplishing this.

In all embodiments, the external housing may be surface treated with a biocompatible material to limit clot formation, control cell growth, or improve lubricity. Such materials may include heparin, silicone, parylene, cell tissue monolayers, or other coatings well known to those of ordinary skill in the art.

While the apparatus and method of subject invention have been shown and described with reference to preferred embodiments, those skilled in the art will readily appreciate that changes and/or modifications may be made thereto without departing from the spirit and scope of the subject invention.

Having thus described the invention, we claim:

1. A wireless circuit for an implant comprising:
   a housing including side walls defining a cuboid wherein said housing has a length, width and height dimensions, and wherein the length is greater than the housing's width and height dimensions, and wherein two opposite sides of the housing are open;
   at least one antenna coil wound about a coil axis and positioned within said housing;
   thin walls bonded to the open sides of the housing wherein said coil axis is substantially parallel to the thin walls of said housing and perpendicular to said length of said housing;
   wherein said thin walls are thinner than the side walls of said housing.

2. The wireless circuit of claim 1, further comprising a pressure sensor that is configured to measure pressure.

3. The wireless circuit of claim 2, wherein said thin walls are configured to deform in proportion to pressure exerted on the thin walls.

4. The wireless circuit of claim 1, further comprising a battery.

5. The wireless circuit of claim 1, wherein said thin walls further comprise a material selected from a group including: sapphire, fused silica, quartz, glass, ceramic, titanium, alumina, silicon, diamond, and polymer.

6. The wireless circuit of claim 1, wherein said wireless circuit is created by forming a cavity in at least one part of said housing prior to bonding said thin walls to the open sides of the housing.

7. The wireless circuit of claim 1, wherein said thin walls are modified by thinning at least a portion of said thin walls after the thin walls are bonded to the open sides of the housing.

8. The wireless circuit of claim 1, wherein said thin walls are bonded to the open sides of the housing by a process selected from a group including: laser welding, glass frit bonding, laser frit welding, compression bonding, anodic bonding, eutectic bonding, brazing, or soldering.

9. The wireless circuit of claim 1, further comprising an electronics portion, wherein the electronics portion serves as one of the thin walls bonded to the open sides of said housing.

10. The wireless circuit of claim 1, further comprising a thin film electronics device.

11. The wireless circuit of claim 1, further comprising an electronics portion and a chamber that contains said antenna coil, wherein the electronics portion is disposed in said housing separate from the chamber that contains said antenna coil.

12. The wireless circuit of claim 1, wherein said housing bonded with said thin walls is filled with a substance selected from a group including: liquid, gel, vacuum, inert gas, or air.

13. The wireless circuit of claim 1, wherein said thin walls of said housing have a thickness less than about 0.025 mm, about 0.020 mm, about 0.015 mm, about 0.010 mm, about 0.005 mm, about 0.001 mm and any sized thickness in between.

14. The wireless circuit of claim 1, wherein the side walls of the housing are between about 0.3 mm to about 0.7 mm.

* * * * *